United States Patent
Lewis et al.

(10) Patent No.: US 11,740,221 B2
(45) Date of Patent: Aug. 29, 2023

(54) SMART RAFT SYSTEM AND METHOD FOR MONITORING AND IMPROVING WATER QUALITY TO MITIGATE ALGAL BLOOMS

(71) Applicants: William H. Lewis, Claymont, DE (US); Carlos R. Villamar, Falls Church, VA (US)

(72) Inventors: William H. Lewis, Claymont, DE (US); Carlos R. Villamar, Falls Church, VA (US)

(*) Notice: Subject to any disclaimer, the term of this patent is extended or adjusted under 35 U.S.C. 154(b) by 307 days.

(21) Appl. No.: 17/108,522

(22) Filed: Dec. 1, 2020

(65) Prior Publication Data
US 2021/0164954 A1  Jun. 3, 2021

Related U.S. Application Data

(60) Provisional application No. 62/991,585, filed on Mar. 18, 2020, provisional application No. 62/943,142, filed on Dec. 3, 2019.

(51) Int. Cl.
*G01N 33/18* (2006.01)
*A01G 9/02* (2018.01)

(52) U.S. Cl.
CPC ........... *G01N 33/1886* (2013.01); *A01G 9/02* (2013.01)

(58) Field of Classification Search
CPC .............................. G01N 33/1886; A01G 9/02
See application file for complete search history.

(56) References Cited

U.S. PATENT DOCUMENTS

| 5,524,549 | A | 6/1996 | Morris |
| 6,694,910 | B1 | 2/2004 | Sharapov |
| 3,327,579 | A1 | 12/2012 | Kania et al. |
| 9,927,529 | B2 * | 3/2018 | Morin ................ G01S 19/42 |
| 2003/0061754 | A1 * | 4/2003 | Cicoff .............. A01M 31/06 43/2 |

(Continued)

FOREIGN PATENT DOCUMENTS

EP  0737418 A2  10/1996

OTHER PUBLICATIONS

Screen captures from YouTube video clip entitled "Captain Drew and the Mushroom Boat" 1 pages, uploaded on Jan. 16, 2013 by user "Ecovative Design". Retrieved from Internet: <https://www.youtube.com/watch?v=u653n4Vv7fw>. (Year: 2013).*

(Continued)

*Primary Examiner* — Magdalena Topolski
*Assistant Examiner* — Edgar Reyes
(74) *Attorney, Agent, or Firm* — Carlos R. Villamar; The Villamar Firm PLLC

(57) ABSTRACT

A system, method and computer program product for monitoring and improving water quality to mitigate harmful algal blooms using smart rafts, including a raft made from a mycomaterial; one or more tube-shaped pods formed in the raft and configured to hold seed or media and configured with a root channel at the bottom of the pods extending through a bottom of the raft; and a sensor holder formed in the raft and configured to hold a water quality sensor accessing a water channel extending through a bottom of the raft. Remedial plants are grown in the tube-shaped pods with roots of the remedial plants passing through the water channel into water underneath the raft.

13 Claims, 9 Drawing Sheets

(56) References Cited

U.S. PATENT DOCUMENTS

| | | | | |
|---|---|---|---|---|
| 2012/0198761 A1* | 8/2012 | Cooke | .................... | A01G 33/00 |
| | | | | 47/1.4 |
| 2013/0168304 A1* | 7/2013 | Kania | .................... | C02F 1/001 |
| | | | | 210/170.05 |
| 2015/0346726 A1* | 12/2015 | Davoodi | ................. | B63B 22/20 |
| | | | | 440/38 |
| 2016/0018339 A1* | 1/2016 | Perkins | .............. | G01N 33/1886 |
| | | | | 73/61.48 |
| 2016/0135396 A1* | 5/2016 | Day | ....................... | A01G 31/02 |
| | | | | 700/275 |
| 2016/0227720 A1* | 8/2016 | Villalon | ................. | A01G 31/02 |
| 2018/0302170 A1* | 10/2018 | Sumption | .............. | G01N 29/00 |
| 2019/0216030 A1* | 7/2019 | Myers | .................... | A01G 33/00 |
| 2019/0281778 A1* | 9/2019 | Hawley-Weld | ...... | A01G 9/0295 |

OTHER PUBLICATIONS

BioHaven Floating Island Technology, © 2009 Copyright. BioHaven, available on the world wide web at http://www.biohavenenvironmental.com/technology.php.

* cited by examiner

SMART RAFT SYSTEM AND METHOD FOR MONITORING AND IMPROVING WATER QUALITY TO MITIGATE ALGAL BLOOMS

CROSS REFERENCE TO RELATED DOCUMENTS

The present invention claims priority to U.S. Provisional Patent Application Ser. Nos. 62/991,585 of RILEY et al., entitled "SMART RAFT SYSTEM AND METHOD FOR MITIGATING ALGAE BLOOMS," filed 18 Mar. 2020, and 62/943,142 of RILEY et al., entitled "SMART RAFT SYSTEM AND METHOD FOR MITIGATING ALGAE BLOOMS," filed 3 Dec. 2019, the entire disclosures of all of which are hereby incorporated by reference herein.

BACKGROUND OF THE INVENTION

Field of the Invention

The present invention generally relates to systems and methods monitoring and improving water quality to mitigate algal blooms, and the like, using smart rafts, and the like.

Discussion of the Background

In recent years, systems and methods for the on-site or in situ mitigating of pollution impairing water quality have been developed. However, such systems typically are lacking in effective mitigation of problematic water quality conditions and the harmful algal blooms that they often cause, and the like, in an efficient and cost-effective manner.

SUMMARY OF THE INVENTION

Therefore, there is a need for a method and system that addresses the above and other problems. The above and other problems are addressed by the illustrative embodiments of the present invention, which provide systems and methods for monitoring and improving water quality to mitigate harmful algal blooms, and the like, using smart rafts, and the like.

Accordingly, in illustrative aspects of the present invention there is provided a system, method and computer program product for monitoring and improving water quality to mitigate harmful algal blooms using smart rafts, including a raft made from a mycomaterial; one or more tube-shaped pods formed in the raft and configured to hold seed or media and configured with a root channel at the bottom of the pods extending through a bottom of the raft; and a sensor holder formed in the raft and configured to hold a water quality sensor accessing a water channel extending through a bottom of the raft. Remedial plants are grown in the tube-shaped pods with roots of the remedial plants passing through the water channel into water underneath the raft.

The system, method and computer program product can include a surface camera mounted in top of the raft for providing one of media documentation, surveillance, and status information.

The system, method and computer program product can include an underwater camera mounted underneath the raft for providing visual information of water quality.

The system, method and computer program product can include one or more solar panels mounted on the raft serving as a power source for electronic elements.

The system, method and computer program product can include a global positioning system (GPS) mounted on the raft providing positional information.

The system, method and computer program product can include a motor mounted on the raft to drive a propulsion system to actively move and position of the raft.

The system, method and computer program product can include a propulsion system mounted on the raft to provide for controlled movement of the raft.

The system, method and computer program product can include a rudder to steer the raft into desired positions.

The system, method and computer program product can include a coupling device to allow one or more rafts to be connected and disconnected to one another.

The system, method and computer program product can include one or more rafts deployed across a body of water to evaluate water quality conditions.

The system, method and computer program product can include one or more rafts deployed in targeted locations within a body of water to improve water quality conditions.

The system, method and computer program product can include an array of the rafts deployed under direction of one or more sampling drones.

Still other aspects, features, and advantages of the present invention are readily apparent from the following detailed description, by illustrating a number of illustrative embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which:

FIGS. 1-2 are diagrams for describing illustrative systems and methods for monitoring and improving water quality to mitigate algal blooms, and the like, using smart rafts, and the like;

DETAILED DESCRIPTION OF THE PREFERRED EMBODIMENTS

Figure 1:
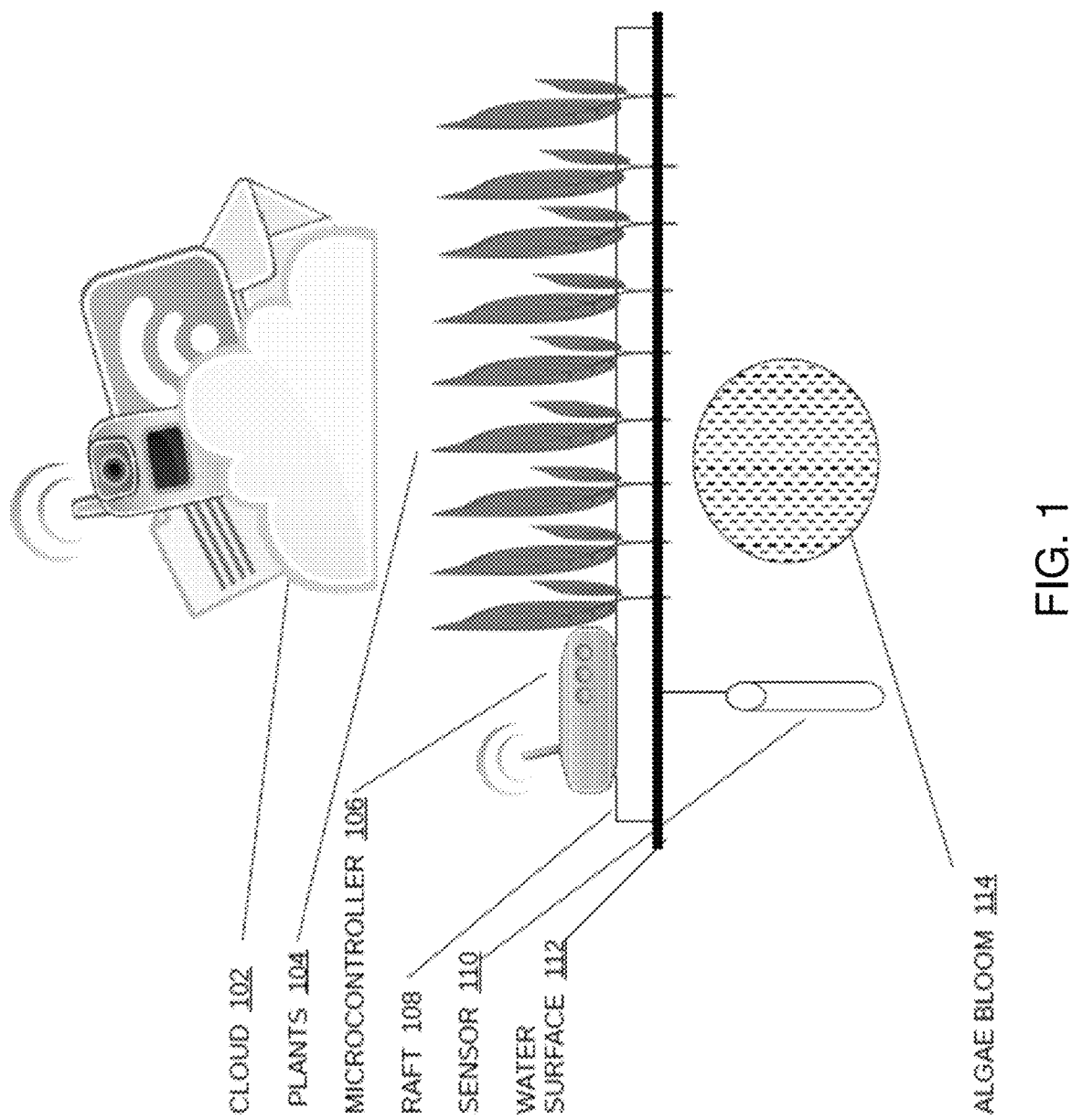

The present invention is directed to developing and deploying an array of biocompatible, biodegradable, and the like, "smart rafts" for monitoring and improving water quality, and the like, within bodies of water, and the like, that are prone to harmful algal blooms, and the like, to mitigate the impacts of urban and agricultural runoff, and the like. The rafts can be constructed, for example, from a novel media substrate, which can be a combination of perlite, biochar, partially decomposed plant matter, a biobased binder, polymer, and the like. For example, halophytic marsh-grass, and the like, of the genus *Spartina, Distichlis, Trigiochin, Pluchea, Grindelia*, and the like, is transplanted into the rafts. Marsh grass of these varieties have been successfully used for phytoremediation of oil (see, e.g., Ogbo, Erute Magdalene, Mary Zibigha, and Gloria Odogu. "The effect of crude oil on growth of the weed (*Paspalum scrobiculatum* L.)-phytoremediation potential of the plant," African Journal of Environmental Science and Technology 3.9 (2009), incorporated by reference herein) and nitrogen contamination (see, e.g., Wright, A. L., R. W. Weaver, and J. W. Webb. "Oil bioremediation in salt march mesocosms as influenced by N and P fertilization, flooding, and season," Water, Air, and Soil Pollution 95.1-4 (1997): 179-191, incorporated by reference herein). Additionally, grass plugs, seeds, and the like, are pretreated with a plant growth promoting bacteria, such as (PGPR) *Burkholderia phytofirmans*, and the like. PGPR are well studied microbes known to increase plant tolerance to stress from salt (see, e.g., Bal, Himadri Bhusan, et al. "Isolation of ACC deaminase producing PGPR from rice rhizosphere and evaluating their plant growth promoting activity under salt stress," Plant and soil 366.1-2 (2013): 93-105; and Akhtar, Saqib Saleem, et al. "Interactive effect of biochar and plant growth-promoting bacterial endophytes on ameliorating salinity stress in maize," Functional Plant Biology 42.8 (2015): 770-781, incorporated by reference herein) as well as industrial pollutants (see, e.g., Afzal, Muhammad, et al. "Inoculation method affects colonization and activity of *Burkholderia phytofirmans* PsJN during phytoremediation of diesel-contaminated soil," International Biodeterioration & Biodegradation 85 (2013): 331-336; and Hou, Jinyu, et al. "PGPR enhanced phytoremediation of petroleum contaminated soil and rhizosphere microbial community response," Chemosphere 138 (2015): 592-598, incorporated by reference herein).

Each smart raft is equipped with a water quality sensor (e.g.; a nitrate ion sensor), and the like, connected to a microcontroller that remotely logs data by accessing the internet, and the like, for example, via T-Mobile's GSM network, and the like. smart rafts can be configured with additional smart design elements including global positioning system (GPS), motor, propeller, and rudder system, and the like, powered by an array of solar panels, and the like, to allow the rafts to be deployed at specific locations. Additional elements, for example, a coupling device, such as mechanical or robotic arms or magnetic couplers, and the like, can be included to connect multiple smart rafts in a line or cluster to provide additional stability or target a water quality condition of concern, and the like, and as further described with respect to FIG. 7.

Water quality data can be logged on any suitable platform, such as Thingspeak.com, and the like, where each smart raft includes a communications channel upon which the gathered data can be charted and analyzed, and the like, for example, using Matlab's suite of tools, and the like. The communications channels can be accessed publicly or privately, and various triggers, and the like, can be programmed to send alerts, for example, via IFTTT.com's mobile application, and the like.

Once an adequate database is established, the database can be supplemented with other datasets, such as levels of precipitation, temperature, tides, and the like. The data can then be uploaded, for example, to Matlab's artificial neural network, and the like, to create forecasting models to ensure that the rafts are deployed in sufficient quantities and at desired locations given observed and forecasted conditions. smart rafts may be deployed in the "evaluation phase" at set distances or arrays across a water body of interest to characterize water quality conditions, and the like, as further described with respect to FIG. 8 or the "treatment phase" with rafts clustered to address an area with impaired water quality or a persistent source, as further described with respect to FIG. 9. Additional "dumb rafts" can be utilized to increase the area of nutrient or other pollutant absorbing biotized marsh grasses; thus, advantageously, improving the efficacy of the invention.

The smart raft, for example, produces real-time and recorded data, and the like, of the water quality conditions (e.g.; nitrate concentrations), and the like, at different inland, coastal and marine locations, and the like, in a cost-effective manner. Advantageously, the recorded data can be used to determine the impact of various human and non-human activities, and the like, on the water quality of inland, coastal, and marine environments, and the like. Results can then be used to develop dynamic management strategies or regulatory approaches, and the like, to address the release of pollutants of concern, and the like, and mitigate their impact on key environmental and cultural resources such as recreation, fisheries, or charismatic species (e.g.; dolphins) and the like.

Figure 2:
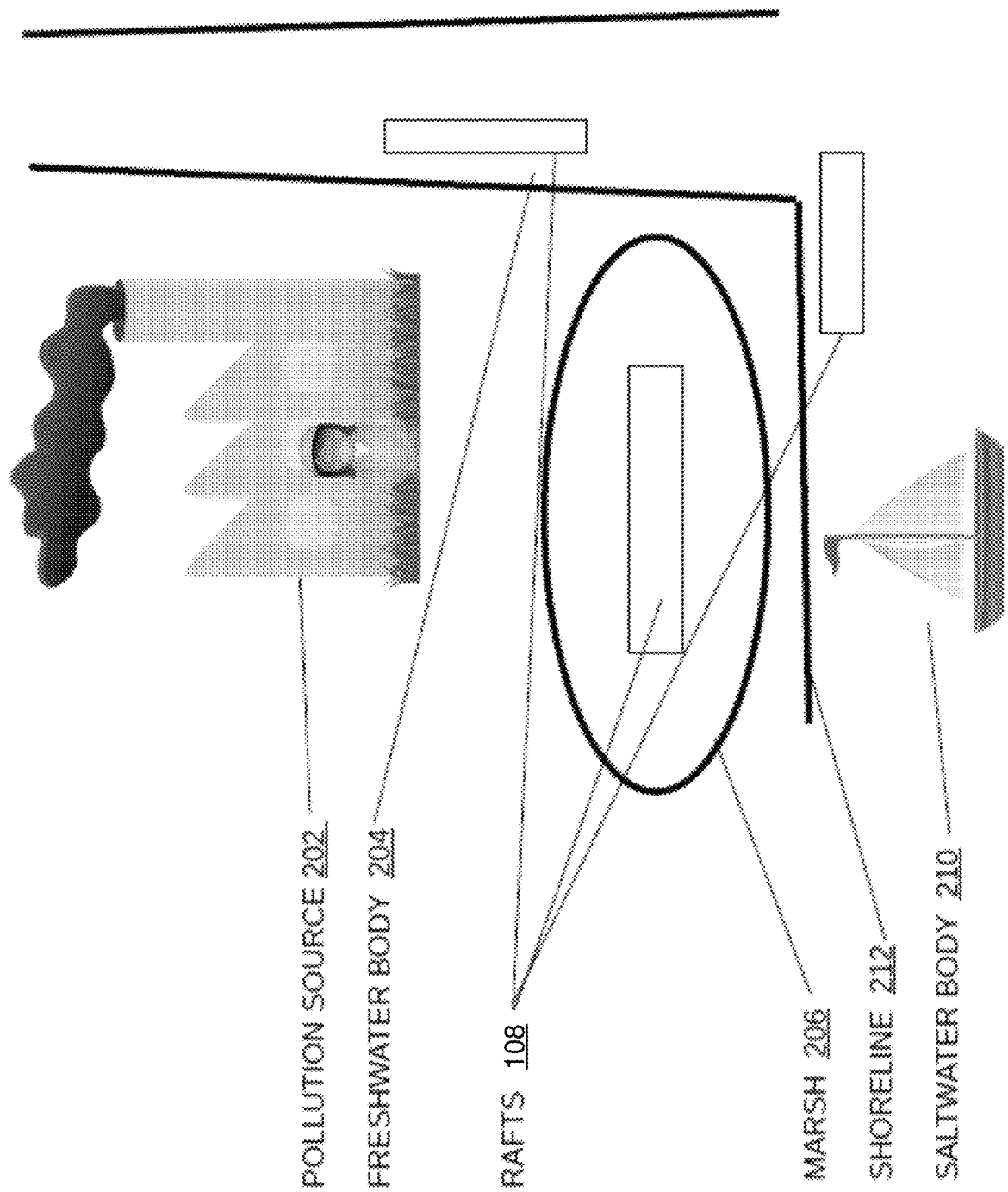

Referring now to the drawings, wherein like reference numerals designate identical or corresponding parts throughout the several views, and more particularly to FIGS. 1-2 thereof, there is shown systems and methods for monitoring and improving water quality to mitigate algal blooms, and the like, using smart rafts, and the like.

In FIG. 1, there is illustrated a side view of a smart raft floating device upon which plants are cultivated for the purpose of phytoremediation of bodies of water with impaired water quality from pollutants such as nutrients and other contaminants that cause harmful algal blooms, and the like. Attached to raft 108 is microcontroller 106, sensor 110, and plants 104. The microcontroller 106 receives voltage from the sensor 110 and processes the sensor voltage reading with a software program. The microcontroller 106 wirelessly connects to the cloud 102 and records the resulting software program data, that is representative of the water condition, in a database. The plants 104 grow within a substrate on top of the raft 108 and the roots penetrate through raft 108 where they make contact with water surface 112 and extract nutrients and contaminants, thus, advantageously, hampering the growth of algae bloom 114.

In FIG. 2, there is illustrated a top view of typical littoral and riparian usage cases, where the rafts 108 can be deployed to remediate pollution sources 202 from human activities, such as agriculture, industry, energy production, and recreation, and the like. Advantageously, the rafts 108 can be dynamically positioned in inland, coastal, or marine water bodies 204 to establish water quality conditions during the "evaluation phase" and at source or inlet of the pollutant of concern or area experiencing impaired water quality within the marsh 206, saltwater body 210, or shoreline 212, and the like.

Accordingly, development and deployment of an array of biodegradable rafts 108 is possible for monitoring water quality and mitigating impaired conditions due to urban and agricultural sources and runoff, and the like. The rafts 108 combine cutting edge phytoremediation biotechnology with affordable electronic sensor technology 110, and the like. Each of the rafts 108 can function simultaneously, for example, as a pollution monitoring and remediation device, and the like. Remediation can be achieved using native wetland plants treated with customized beneficial bacteria, and the like, as previously and further described. Monitoring can be achieved using low cost intelligent sensors 110, and the like. The collected data can be used to weave into a data visualization and environmental informatics platform to effectively convey water quality conditions to public, private and civil society stakeholders, and the like, in regions where bodies of water are prone to impaired water quality such as elevated nutrient concentrations the lead to harmful algal blooms, and the like. Targeted site locations can include agricultural, municipal and industrial point and nonpoint sources, and the like.

The rafts 108 can be part of comprehensive and integrated strategy for the development, prototyping, and creation of an interface platform for regenerative marine infrastructure deployment, and the like. In this context, the rafts 108 can be strategically deployed in both "evaluation" and "treatment" phases that can be readily summarized in data visualization dashboards or multi-stakeholder design charrettes to rapidly prototype a public/private tool set for improving water quality and restoring at-risk marine and freshwater habitats, and the like. The invention employs the intersectional functionality of a low-cost water quality sensors with living shoreline technologies to support the on-site or in situ treatment of pollutants of concern (e.g.; nitrate), and the like.

Through expansion of technology partnerships and cultivation of a public/private engagement platform, the invention can be focused on concerted and technical scaling for large-scale nutrient harvesting at watershed scale. The invention can create an integrated solution set of technologies, that integrates hardware and software development with ecological and culture specific strategies that can not only meet the challenge of impaired water quality and the harmful algae blooms that they cause worldwide, but can also cultivate the relationship between ocean health, blue carbon, and high-protein biomass that can supply the exploding market for plant-based meats, food supplements, and animal feed, and the like.

The public/private partnership approach is a management strategy focused on more effectively quantifying, aggregating, and communicating the adverse impact on the environmental, cultural, and economic resources of, for example, the Gulf Coast of the United States. In this way, galvanization and support from all suitable stakeholders can be achieved, for example, to more effectively manage nitrate sources in the Mississippi River watershed, and the like. Adoption of such comprehensive solution sets can include a range of effective initiatives, like a novel nutrient trading framework, agricultural subsidies to implement contour farming, and transitioning of wastewater treatment plants into water recycling plants, and the like. The invention can be used to develop, for example, a Phase 1 Environmental Site Assessment (ESA) equivalent for inland, coastal, and marine ecosystems which can address: Permitted, unpermitted, and legacy discharges into the water bodies that may compromise ecosystem health; Adaptation of techniques and initiatives from terrestrial analogs, for example, Communities that are reclaiming underutilized or abandoned lots for urban gardens; Brownfield remediation efforts that address site soil conditions characterized by high concentrations of heavy metals, chlorinated compounds, or other hazardous materials that affect human health; Community garden programs that improve soil health and manage risk after a Phase I ESA; water body condition monitoring programs that help ensure water and sediment quality aligns with intended uses (e.g. assessing microbial conditions that are safe for swimming and shellfish consumption); and Measuring and monitoring toxic chemical concentrations and harmful algal blooms that impact shellfish health and aquaculture activities; and the like.

In order to prevent the formation of harmful algal blooms, a comprehensive program to address both point and non-point source nutrient discharges from urban and agricultural sources must be developed and implemented. A key component of such an effort is characterizing riverine and marine nutrient conditions to allow for the tracking and identification of key sources or source areas. Accordingly, the rafts 108 can be deployed along water bodies of all sized (e.g.; the Mississippi River watershed) to address this key data gap and allow for the management of true nitrate sources with novel, paradigm shifting strategies and solutions. The water quality sensors 112 can both help to identify where these discharges are occurring, as well as how much uptake is occurring from the aquatic grasses 104 integral to the rafts 108.

The present invention builds on experience prototyping floating islands and commercial aquaponics, and intensive study of the millennia old tradition of chinampas "floating agriculture" in Mexico City, to create several raft deployment strategies, as described herein. The invention can include use of mobile containment booms, both synthetic and biodegradable, (e.g., treated with biocompatible water repellant to modulate longevity, etc.) as buoyancy to receive aggregations of invasive species that are piled onto, or woven around substrates of biochar, hyper-buoyant pumice and/or bulky perlite (e.g., contingent on local availability). Bamboo, or similar lattices can be employed to keep or contain the substrate subsurface, as rhizosphere generates. The biochar matrix employed functions as a biodegradable planting bed for regionally selected native wetland species, allowing roots to penetrate into the water column, while also providing water remediation benefits and providing rhizogenic habitat. Over a period of years, the biochar can become increasingly water-logged, but can still capacitate a high level of hydraulic conductivity. The root mass of the wetland plants 104 can also mitigate the tendency for the lattice to slowly disintegrate. New invasive species biomass can be added periodically to compensate for the sinking water level. The modular raft 108 design can employ a non-reactive marine foam matrix for buoyancy. This model is for locations in deeper water, where the roots are unable to attach to the benthos and where jurisdictional requirements demand long term functionality.

General design criterion for the rafts 108 includes: The use of biodegradable materials which, in case they break up in a storm or flood event, will damage neither the local environment where they were deployed, nor downstream ecotones; A flexible module raft substructure that can be grouped and easily relocated and/or designed to be unfurled from a spiral and deployed as bank stabilization or coastal protection; A mix of 'dumb' and 'smart' rafts that maximize nutrient uptake at key point source pollution locations, while minimizing the cost and risk for damage to the 'smart' sensor components of the rafts; Location dependent landscape design that is aesthetically pleasing and/or visually blends into the local biome. Selected raft deployments may also function as floating art installations or creative learning laboratory installations; Photo and video capture of both the rafts 108 in action and polluted areas before and after nutrient or other pollutant uptake using strategically placed cameras; Tamper resistant tethering and platform design that discourages vandalism.

The rafts 108 construction can incorporate a customized media blend that combines pumice perlite, mushroom material, biochar and partially decomposed plant matter. Halophytic marsh-grass of the genus *Spartina* can be transplanted into the rafts. *Spartina* species have been successfully used for phytoremediation of both oil (see, e.g., Wright, A. L., R. W. Weaver, and J. W. Webb. "Oil bioremediation in salt march mesocosms as influenced by N and P fertilization, flooding, and season." Water, Air, and Soil Pollution 95.1-4 (1997): 179-191, incorporated by reference herein) and nitrogen contamination (see, e.g., Bhatia, Misha, and Dinesh Goyal. "Analyzing remediation potential of wastewater through wetland plants: a review." Environmental Progress & Sustainable Energy 33.1 (2014): 9-27, incorporated by reference herein). Plants can be purchased as plugs (e.g., seedlings). Before insertion of plugs into the raft 108 media, their roots can be pretreated with the plant-growth-promoting bacteria (PGPR) *Burkholderia phytofirmans*. PGPR are well-studied microbes known to increase plant tolerance to stress from salt (see, e.g., Bal, Himadri Bhusan, et al. "Isolation of ACC deaminase producing PGPR from rice rhizosphere and evaluating their plant growth promoting activity under salt stress." Plant and soil 366.1-2 (2013): 93-105; and Akhtar, Saqib Saleem, et al. "Interactive effect of biochar and plant growth-promoting bacterial endophytes on ameliorating salinity stress in maize." Functional Plant Biology 42.8 (2015): 770-781, incorporated by reference herein) and industrial pollutants (see, e.g., Bal, Afzal, Muhammad, et al. "Inoculation method affects colonization and activity of *Burkholderia phytofirmans* PsJN during phytoremediation of diesel-contaminated soil." International Biodeterioration & Biodegradation 85 (2013): 331-336; and Hou, Jinyu, et al. "PGPR enhanced phytoremediation of petroleum contaminated soil and rhizosphere microbial community response." Chemosphere 138 (2015): 592-598, incorporated by reference herein). Among PGPR, *Burkholderia phytofirmans* represents an ideal candidate due to its extremely low risk to both environmental and human safety. *B. phytofirmans* is a plant growth promoting bacteria which is naturally occurring in soils. The genome of *B. phytofirmans* has been fully characterized and proven to lack important pathogenicity factors necessary for causing disease in humans (see, e.g., Mitter, Birgit, et al. "Comparative genome analysis of *Burkholderia phytofirmans* PsJN reveals a wide spectrum of endophytic lifestyles based on interaction strategies with host plants." Frontiers in plant science 4 (2013): 120, incorporated by reference herein). Such bacteria enter the internal tissues of plants granting its host resistance to stressors by mechanisms common to many PGPR including growth hormone production (see, e.g., Kurepin, Leonid V., et al. "*Burkholderia phytofirmans*-induced shoot and root growth promotion is associated with endogenous changes in plant growth hormone levels." Plant growth regulation 75.1 (2015): 199-207, incorporated by reference herein) and stress hormone reduction (see, e.g., Sun, Yili, Zhenyu Cheng, and Bernard R. Glick. "The presence of a 1-aminocyclopropane-1-carboxylate (ACC) deaminase deletion mutation alters the physiology of the endophytic plant growth-promoting bacterium *Burkholderia phytofirmans* PsJN." FEMS microbiology letters 296.1 (2009): 131-136, incorporated by reference herein). Since not all plant-microbial associations are beneficial or even functional, our research teams have already conducted preliminary inoculation tests. During these tests researchers were able to inoculate *Spartina alterniflora* seedlings with *B. phytofirmans*, observe healthy growth under saline conditions and then re-isolate the bacteria from inside sterilized plant tissues. Such test used by microbiologists and confirms both infection and establishment within the plant by the bacteria. More importantly, it rules out potential negative interactions between the plant and bacteria which, although not likely, are possible.

Each of the rafts 108 can be equipped with a water quality sensor (e.g.; nitrate ion sensor) 110. Each sensor 110 can be connected to a microcontroller that remotely logs data by accessing the internet via T-Mobile's GSM network. The data can be logged on Thingspeak.com, where each raft's 108 sensor 110 can have an exclusive channel for which the data can be charted and analyzed with Matlab's suite of tools. The channels can be set to be accessed publicly or privately. Triggers can be programmed to send alerts via IFTTT.com's mobile application.

In addition to the standard rafts 108 water quality sensor 110, supplemental data sets can easily be collected (e.g. precipitation levels, temperature, etc.). Additional suites of sensors can also be incorporated into the rafts to monitor phytoextraction and phytostabilization of metals such as cadmium, lead, zinc and copper (e.g. in areas where dredging or runoff is releasing these pollutants into the water column). The data can then be uploaded to Matlab's artificial neural network to create forecasting models to ensure that the rafts are deployed in sufficient quantities. In addition to the rafts 108, "dumb rafts" without sensors can be utilized as needed to increase the area of nutrient-absorbing, biotized marsh grasses; thus, improving the efficacy of the rafts' remediation function.

After deployment of the rafts 108, economically deploying larger individual systems, as well as expanding the number of deployment types and locations will proceed. An example application would be characterizing the marine environment of the Mississippi Bight to establish the variability of nitrate concentrations and the well-publized low oxygen "dead zone" over space and time. smart rafts could be deployed in the "evaluation phase" at set distances or arrays across a water body of interest to characterize water quality conditions, and the like, or the "treatment phase" with rafts clustered to address an area with impaired water quality or a persistant source. Once these currently poorly understood dynamics are effectively characterized, deploying a network of rafts 108 upstream through the Mississippi River Watershed to identify tributaries with elevated nitrate concentrations could proceed. Existing and additional rafts 108 arrays can then be positioned to identify specific significant point and nonpoint nitrate sources of nitrate. The rafts 108 array can be supplemented with "dumb rafts and deployed in optimized locations to intercept the maximum amount of nitrate and other nutrients without interfering with riverine or marine navigation. Wherever possible, rafts 108 can be deployed close to shore and in bays, inlets, or other protected areas with minimal watercraft traffic. As part of the community engagement and grassroots mobilization component of such initiatives, raft 108 deployments can be matched with local individuals or aligned organizations that can take on the important work of stewardship and observation of the rafts, helping to identify when rafts move out of place, malfunction, or experience vandalization.

As an impact-oriented endeavor, there is an opportunity to efficiently combine fabrication economies of scale with local deployment partnerships so as to be able to offer an affordable and effective means of watershed-scale pollution harvesting that delivers measurable downstream benefits. Primary and tertiary benefits would include: Improved water quality (primary measurable and monetizable outcome); aquatic habitat restoration; safer drinking water; improved public health; carbon sequestration; river bank and levy reinforcement; and reduced stress on ocean ecosystems.

Though some of these benefits are not necessarily easy to quantify or monetize, they are all suitable measurable and demonstrable contributions to the restoration of at-risk river and ocean ecosystems. Furthermore, there is the opportunity to scale the rafts 108 deployment in the context of an evolving suite of technologies that to a greater or lesser degree are associated with the basic rafts 108 prototype technologies. The derivative or complementary mariculture and aquaculture technologies, for which the invention can be employed include: Macroalgae and microalgae farming (for food, food supplements, animal feed, pharmaceuticals, and biofuels); Floating shellfish farms that dramatically improve water quality; Large scale off-shore seaweed farming that incorporates ocean macro systems like upwelling; Floating solar and/or wave energy harvesting; Wastewater treatment wetlands that harvest urban pollution and restore aquatic habitat while building coastal biomass; Coastal protection island and reef systems that harnessing the power of oyster reefs and existing tidal forces; Over-the-horizon offshore wind farms that can provide complementary infrastructure and services for semi-automated mariculture stations.

These systems and technologies are ready to scale but have so far lacked a critical mass of industry support and informed demand. The present invention can accelerate the process of scaling their deployment and impact through an integrated approach that aligns these multiple quantitative and qualitative benefit streams through informed community engagement, education, training, so as to attract and harnesses the growing interest of the investment community in opportunities to finance viable technologies that demonstrate their value for improving planetary health.

The rafts 108 are designed to facilitate efficient and effective real-time data collection of water quality conditions at different aquatic and marine locations in a cost-effective manner. A key localized outcome of a successful prototype rafts 108 design and deployment can be reliable access to tools for a higher quantity and quality of data for locating and monitoring point source pollution and general water quality. The interpreted data can be used to determine the effects of various human activities, for example, on the Mississippi River water and marine environments offshore, as well as track the efficacy of bioremediation efforts. Such information can then be used to guide the formulation of local and regional policy for monitoring and regulating pollution discharge. Increased reliable water quality data collection can facilitate better characterization of baseline conditions. These baseline conditions can be used to identify sources or source areas of concern, compared to relevant regulatory requirements, and allow for the development of novel public/private partnerships such as nutrient trading.

The advantages of the present invention can precipitate the opportunity to realize a wide range of secondary outcomes that can come from the broader deployments of the rafts 108 systems, providing more comprehensive regional (and/or national) data collection coverage, and allowing scientists and regulators to identify, respond to, and monitor pollution hot spots. Empowered with this data and partnered with willing regional organizations, the rafts 108 deployments can facilitate a suite of long-term positive outcomes, including: The ability to track downstream pollution to its upriver point source and identify its cause; Equip farmers and other landowners with better tools for pollution mitigation and sustainable land management; Quantitatively demonstrate the benefits regenerative soil management practices (e.g. no-till, organic pest control, etc.); Broader global understanding of watershed health and protection through shared data platforms, storytelling and open technology sharing; and Expanded partnerships with aligned institutions that can help disseminate lessons learned, apply better solution sets, and finance the rapid scaling of the solution sets needed to address today's climate crisis.

The rafts 108 project can help bring data to life. Too often data gets buried beneath political inertia. Successful rafts 108 deployments can offer rural communities most affected by environmental degradation a suite of tools to monetize the data that proves how floating wetland and associated technologies can restore large scale degraded aquatic ecosystems. Through creating and deploying our IOT smart raft platform into a framework that is ergonomic and simple to interface with for rural workforce development, the invention can achieve interoperability with the best policy and market forces to optimize the full performance potential of our aquatic ecosystems and watershed-based economies.

Figure 3:
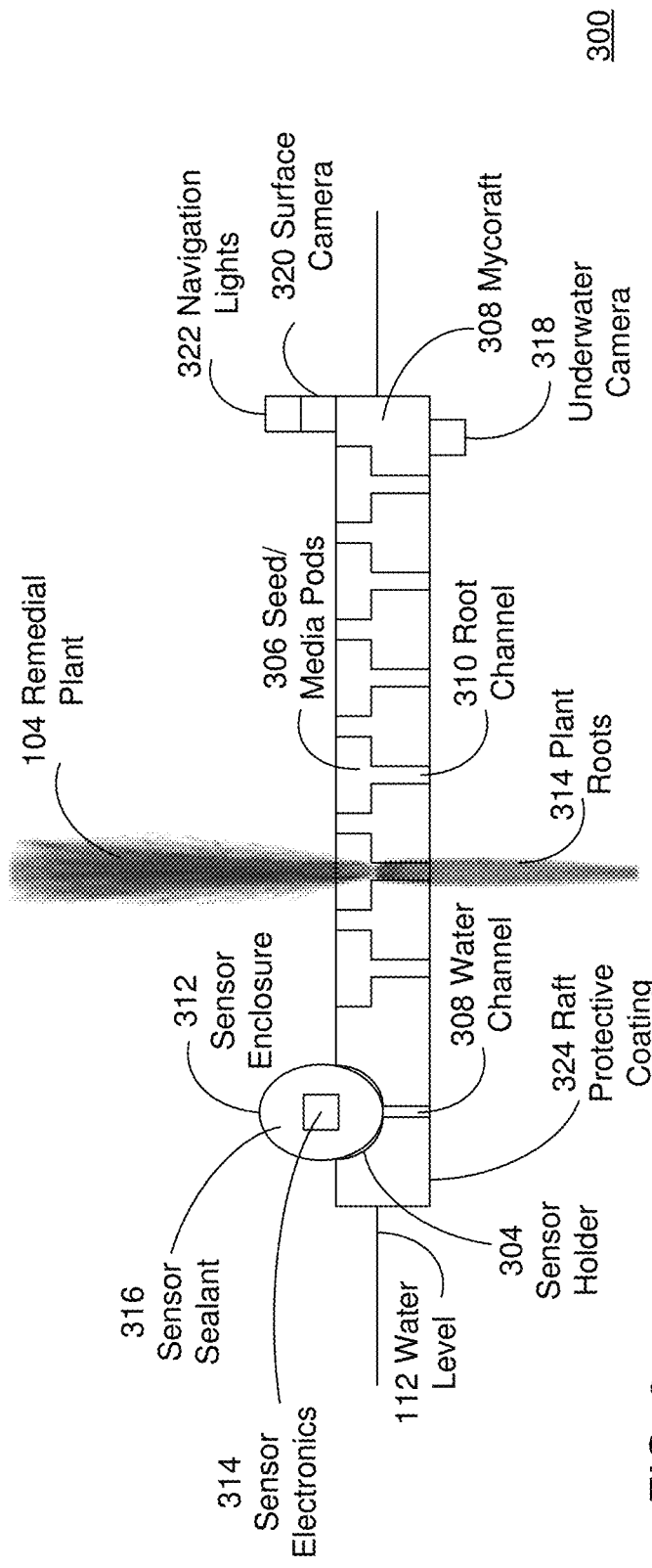
FIG. 3 is a diagram of an illustrative raft design employing mycomaterials.

FIG. 3 is a diagram of an illustrative raft design employing mycomaterials. In FIG. 3, the raft 308 can be made from a mushroom material (e.g., mycomaterial, etc.) using known techniques, and the like, and include seed/media pods 306 with root channels 310, a sensor holder 304 with water channel 308, formed in the mycomaterial. Remedial plants 104 can be grown in the seed/media pods 306 with plant roots 314 passing through channel 310 in to the water. The mycomaterial can be made of a suitable thickness for providing a desired buoyancy with respect to the water level 112. The mushroom material, advantageously, increases buoyancy, and the like. A surface camera 320 (e.g., GoPro, etc.) can be included in at least one raft when a fleet of rafts are employed, and used, for example, for media documentation, surveillance, status, and the like. Similarly, an underwater camera 318 (e.g., GoPro, etc.) can be included, for example, to provide visuals of water quality in contaminated or algal areas, and the like. Navigation lights 322 (e.g., LED, etc.) can be employed, as needed.

The mycoraft 308 can be encased with a protective, waterproof coating 304, and the like, for example, made of hemp plastic material, lignin, and the like, to prevent sudden degradation, and the like. The coating 304 can be configured to be biodegradable at around 6-18 months, and the like, and made to be sustainably produced, and the like, and as further described with respect to FIG. 4.

A sensor enclosure 312 can be used to house sensors and electronics 314, such any suitable electronic circuitry, sensors, batteries, motors, and the like. The sensor enclosure 312 can be made from a hollow coconut shell, gourd or other suitable biodegradable container, and the like, that is readily available, cheap, biodegradable, naturally sourced and the like. The sensor enclosure 312 can be cut or fashioned in such a way at to fit components inside, and then sealed with as sealant 316, such as epoxy resin or other suitable material, and the like, that has desired characteristics, such as being waterproof, salt water stable, fish safe, and the like, for the purpose of protecting the enclosed components from the elements, and the like. Electrical leads and the like can be configured to exit the sensor enclosure 312 for attaching probes, and the like. A water quality sensor can be employed in the electronics 314 and along with addition water quality sensors, such as dissolved oxygen (DO), biological oxygen demand (BOD), pH, and the like, or pollutant uptake can be inferred, by measuring biomass, and the like. Any suitable printed circuit board (PCB) can be made from any suitable bioplastic, and the like. In addition, portable gas and mass spectrometers can be employed to measure liquid and gas parameters (e.g., CO2, O2, pH, DO, nitrates, nitrites, anomia, etc.), as needed, with data logging via a communication network (e.g., by employing sensors from Spectral Engines, as described on the world wide web at www.spectralengines.com and incorporated by reference herein).

Advantageously, the biodegradability of the raft can be modulated with biocompatible coatings 304 so as not to harm an aquatic ecosystem, and the like. The raft 308 can be constructed in the field with abundant and/or invasive species or mass produced and shipped from afar, and the like. Invasive species can be treated or inoculated in any suitable way to prevent unwanted spread, and the like. Water quality data collected can allow for the characterization of existing baseline conditions, and the like. Such baseline conditions can be used to identify sources or source areas of concern, and the like, and compared to relevant regulatory requirements, and the like, to allow for the development of novel public/private partnerships, such as nutrient trading, and the like.

Accordingly, a temporary raft that breaks down or can be removed, and the like, leaving behind a dense root raft, allowing the established roots (or raft) to support the new growth. Such natural rafts can be grown in ponds and once mature released into open water, and the like. The employed mycomaterial, advantageously, automatically sheds chitin fragments into media in the seed/media pods 306, thus eliminating the need for chitinase any inoculum carrier, and the like. By employing mycomaterial, a simpler and cheaper carrier, e.g., peat or coconut coir, and the like, can be employed. The benefit of the mycomaterials thus includes a production of chitin fragments, which trigger a pathogen associated molecular pattern (PAMP) immunity in plants, and the like, and of particular benefit in damp environments, and the like, where fungal pathogens, such as fusarium can be a big problem.

For example, an inoculum employed, for example, can be 10^8-10^6 CFU of *B. phytofirmans* suspended in a phosphate buffer with a mixture of peat and chitosan (5/1) as the microbial carrier. Advantageously, this provides for a long storage carrier for the microbe, for ease of transportation to site, and the like. The chitosan helps with fungal resistance, as it triggers plant immunity, and the like, wherein one can dip or coat the plant 104 roots 314, and the like. In addition, a simpler liquid inoculant can be worked up on site, and the like. The plants 104 can include vetiver grass, and the like.

Achieving an optimal level of buoyancy is desirable. The tethering of the rafts 108 or 308 to smart buoys (not shown), and the like, can be employed, which functions to increase ergonomics or reduce storage and maintenance of smart sensors on the raft, and the like. Such buoys can be reusable with minimal handling, and include navigation lights, and the like. The remedial plants 104 can include saltwater and various freshwater species, selected based on application, and the like. In case of wave action and currents, the rafts 108 can be deployed inside bays, mudflats (e.g., where they simply sit on the mud during low tide, etc.) and the like.

The rafts can be made to any suitable dimensions, to treat a given liters/second of water. The rafts 108 can be linked together to form long booms, and the like. For example, the rafts 108 or 308 can be modular and sized to fit standard pallets 4'×4' for cost efficient shipping and easier handling/installation, and the like, and with a 5 to 10-year lifespan, and the like. Flotation can be improved, for example, by including used PET plastic beverage bottles, and the like, in the structure.

Figure 4:
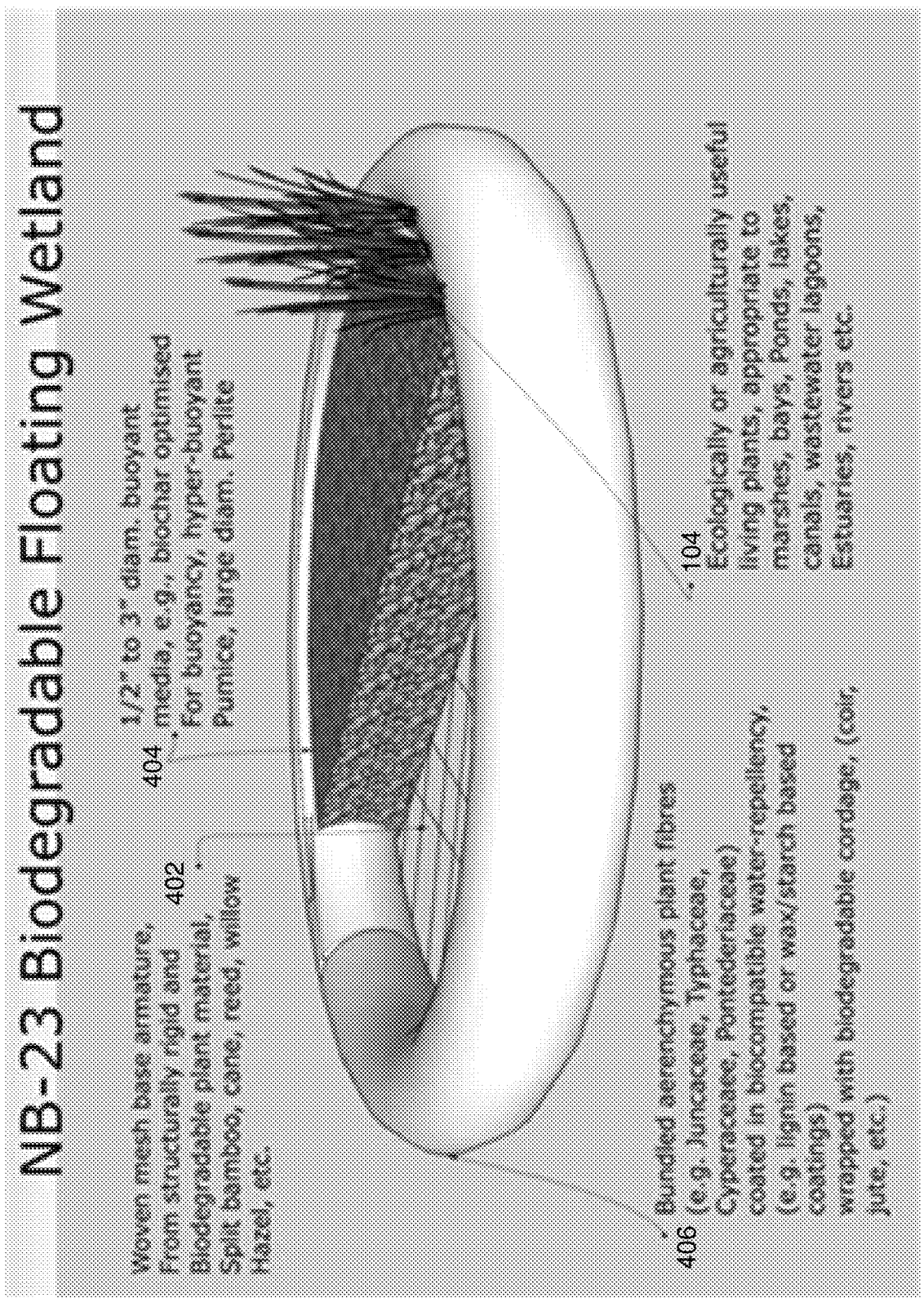
FIG. 4 is a diagram of an illustrative circular raft design.

FIG. 4 is a diagram of an illustrative circular raft design. In FIG. 4, the raft 108 includes a woven mesh base armature 402 is made from, for example, structurally rigid and biodegradable plant material, such as split bamboo, cane, reed, willow, hazel, and the like. Buoyant media 404 can be half inch to 3-inch diameter buoyant media, for example, biochar optimized for buoyancy, hyper-buoyant pumice, large-diameter perlite, and the like. Circular raft support structure 406 can be made, for example, from bundled aerenchymous plant fibers (e.g., Juncaceae, Typhaceae, Cyperaceaee, Pontederiaceae, etc.) coated in biocompatible water repellency coatings (e.g., lignin based or wax/starch-based coatings, etc.) wrapped in biodegradable cordage (e.g., coir, jute, etc.). Employed are ecologically or agriculture useful living plants, for example, appropriate to marshes, bays, ponds, lakes, canals, wastewater lagoons, estuaries, rivers, and the like. The rafts 108 can active, for example, by employing wave, wind power, and the like, to pump surrounding water into perforated hoses at the center of each raft. Accordingly, a rafted wetland can be configured for water treatment, with numerous floating rafts 104 having roots dangling into the water, and increased water treatment capacity can be employed by pumping water into the centers of the rafts 108.

Figure 5:
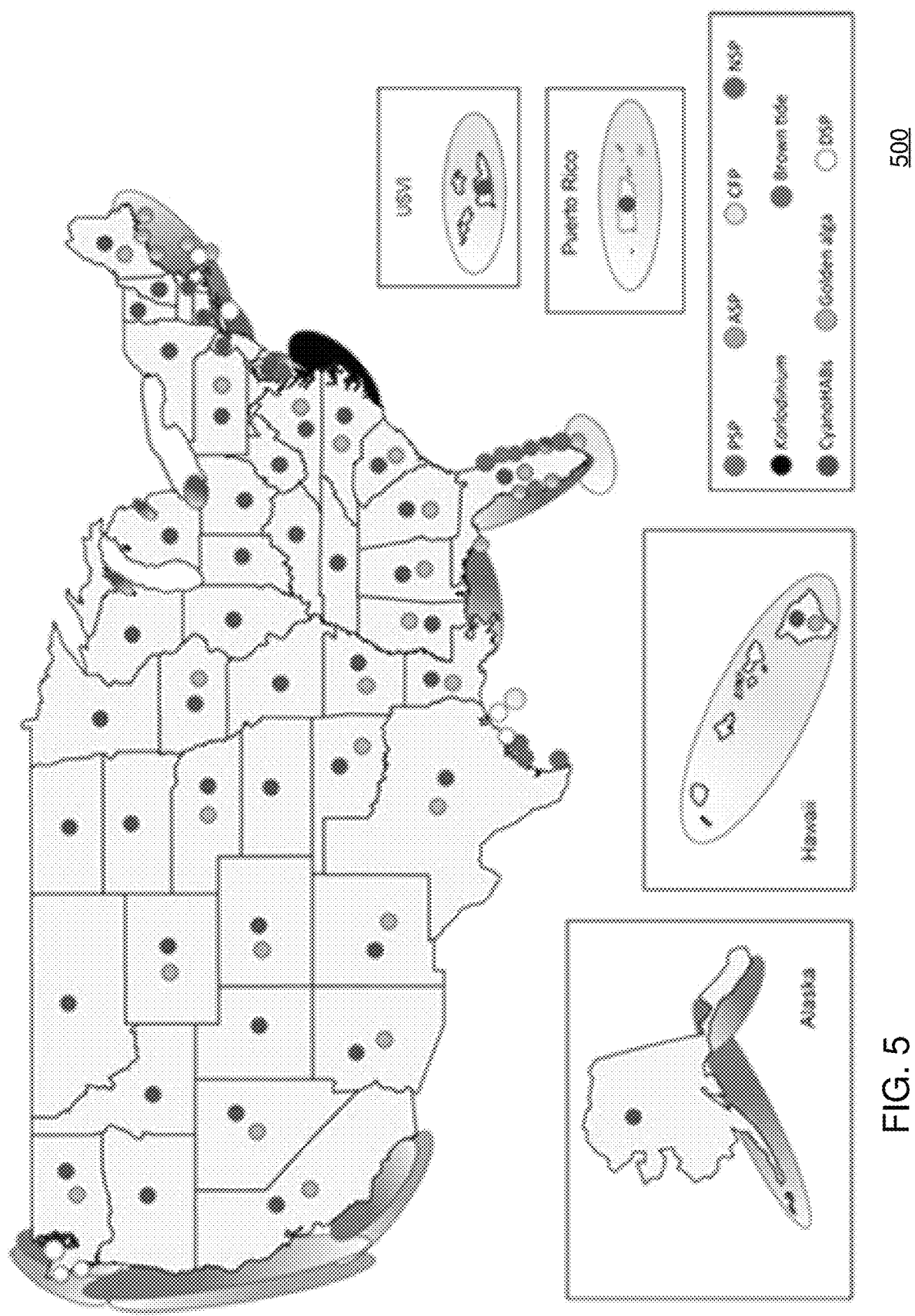
FIG. 5 is generalized view of the U.S. depicting the various HAB poisoning syndromes.
Figure 6:
FIG. 6 is a site option for raft deployment in the U.S. near the confluence of the San Joaquin and Mokelumne Rivers.

FIG. 5 is generalized view of the U.S. depicting the various harmful algal bloom (HAB) poisoning syndromes. In FIG. 5, is shown the various HAB poisoning syndromes and their impacts that occur in specific areas. Dots and ovals indicate locations where the incidence of particular syndrome has been reported or toxins have been detected in tissue extracts are plankton. Ovals are used to indicate regional phenomena that occur at multiple locations along a coastline. All 50 states are impacted by cyanobacteria HAB (cyanoHAB), typically in many different rivers, streams, reservoirs, etc. The same is true for 23 states impacted by golden algae blooms caused by *Prymnesium parvum*. It is not practical to indicate the location of each cyanoHAB or golden algae bloom, so each state experiencing these blooms is indicated using a single dot. Large ovals denote widespread cyanoHAB problems in those areas. FIG. 6 is a site option for raft deployment in the U.S. near the confluence of the San Joaquin and Mokelumne Rivers in California.

Figure 7:
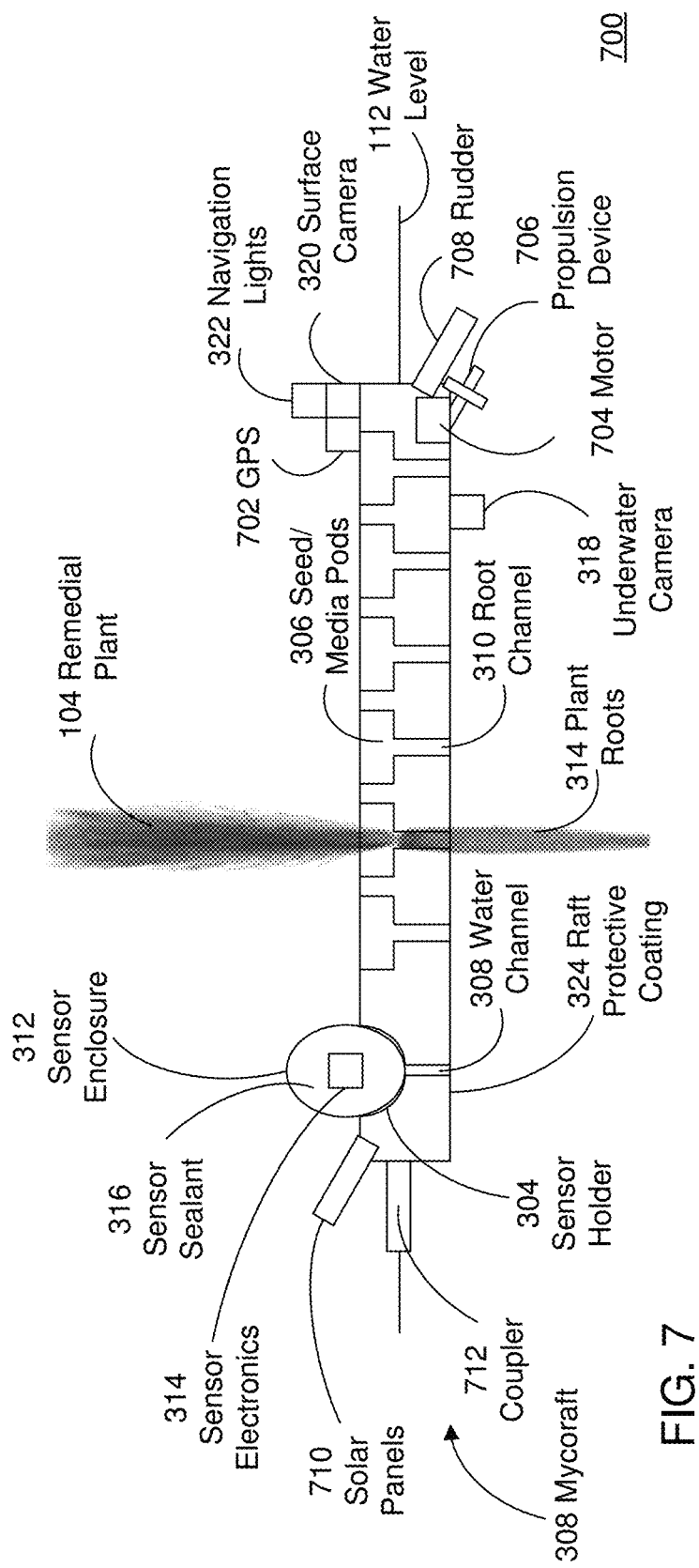
FIG. 7 is a diagram of an enhanced illustrative raft design employing smart elements.

FIG. 7 is a diagram of an enhanced illustrative raft design employing smart elements. In FIG. 7, the system 700 includes an enhanced smart raft 308 configured with additional smart functionality enhancements including global positioning system (GPS) 702, motor 704 and a propulsion device 706, such as a propeller or similar system to drive the raft 308 (e.g; water jet, etc.), and rudder system 708 to steer the raft 308. The GPS, drive, and steering systems are powered by an array of solar panels 710 and allow the rafts to be deployed at specific locations for defined periods of times. A coupling device 712, such as mechanical arms or magnetic couplers, and the like, can be included to connect multiple smart rafts 308. Lines or clusters of smart rafts 308 advantageously provide additional stability during adverse weather conditions, and the like, and allow for the targeting of water quality conditions of concern, and the like.

Figure 8:
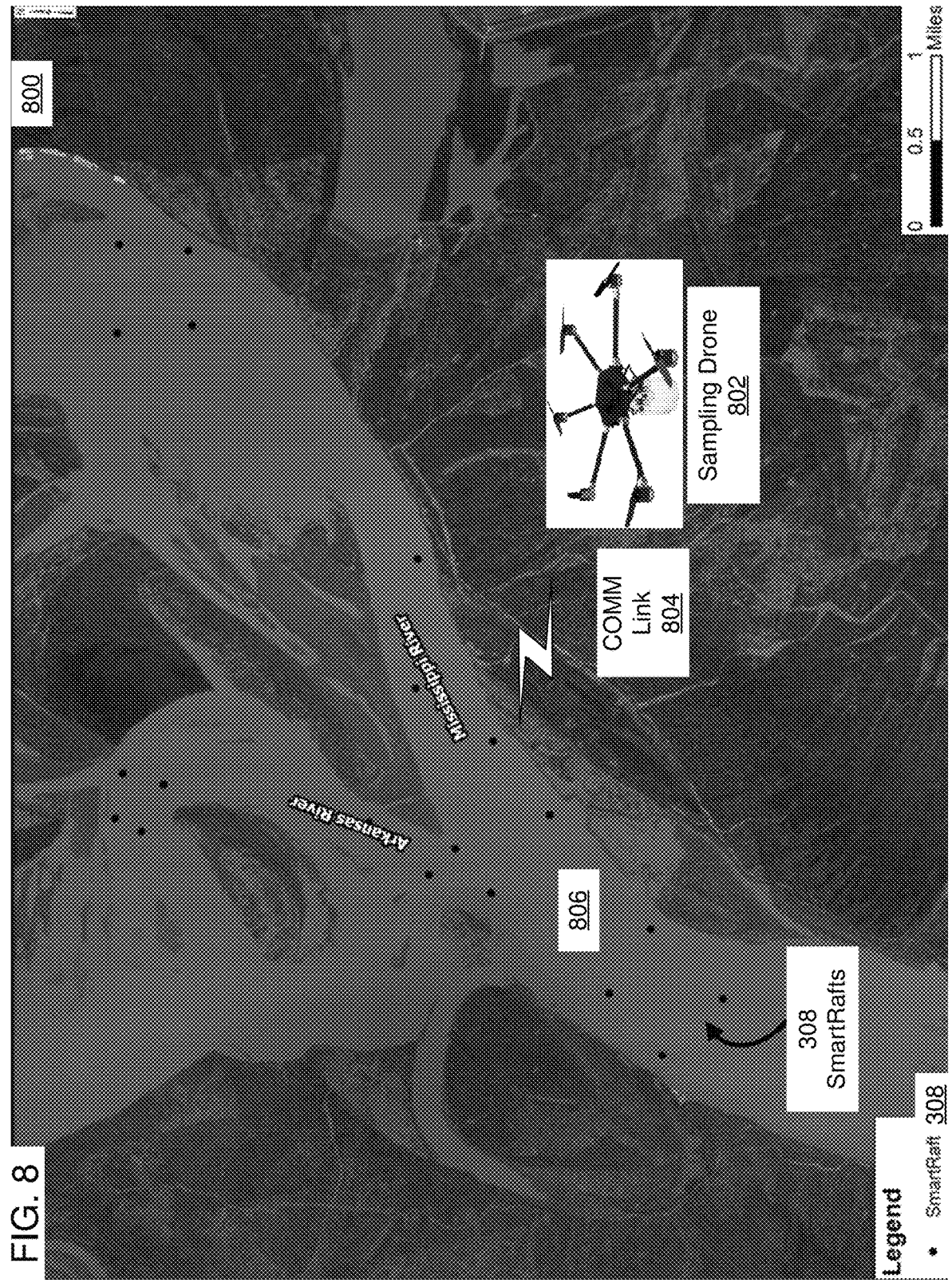
FIG. 8 is a diagram showing an array of smart rafts deployed in the evaluation phase at the direction of a sampling drone.

FIG. 8 is a diagram showing an array of smart rafts deployed in the evaluation phase at the direction of a sampling drone. In FIG. 8, the system 800 includes an array of smart rafts 308 deployed in the "evaluation phase" at the direction of one or more sampling drones 804 over a suitable communication link 804 to establish water quality conditions in a new or unknown aquatic marine environment. The smart rafts 308 are deployed in a grid across a water body 806 to monitor the changes in water quality over space and time. The smart rafts 308 are reporting observed water quality conditions, effectively a variable that can be employed, for example, in a machine learning component, such as Matlab's artificial neural network, and the like. The period of smart raft implementation in the "evaluation phase" can be carried out for the duration that accounts for variability in the water body of interest.

The sampling drones 802 can capture, for example, multiple liquid samples, and the like, in one or more liquid sample receptacles, for example, with a gear drive mechanism, and the like, to lower and raise the liquid sample receptacles into the water body 806 to capture multiple liquid samples for analysis, and the like. Advantageously, the fast-moving sampling drones 802 provides efficient screening of water quality conditions, and the like, and allows for the deployment of the smart rafts 308 in areas where conditions are variable or less understood during the "evaluation phase."

Figure 9:
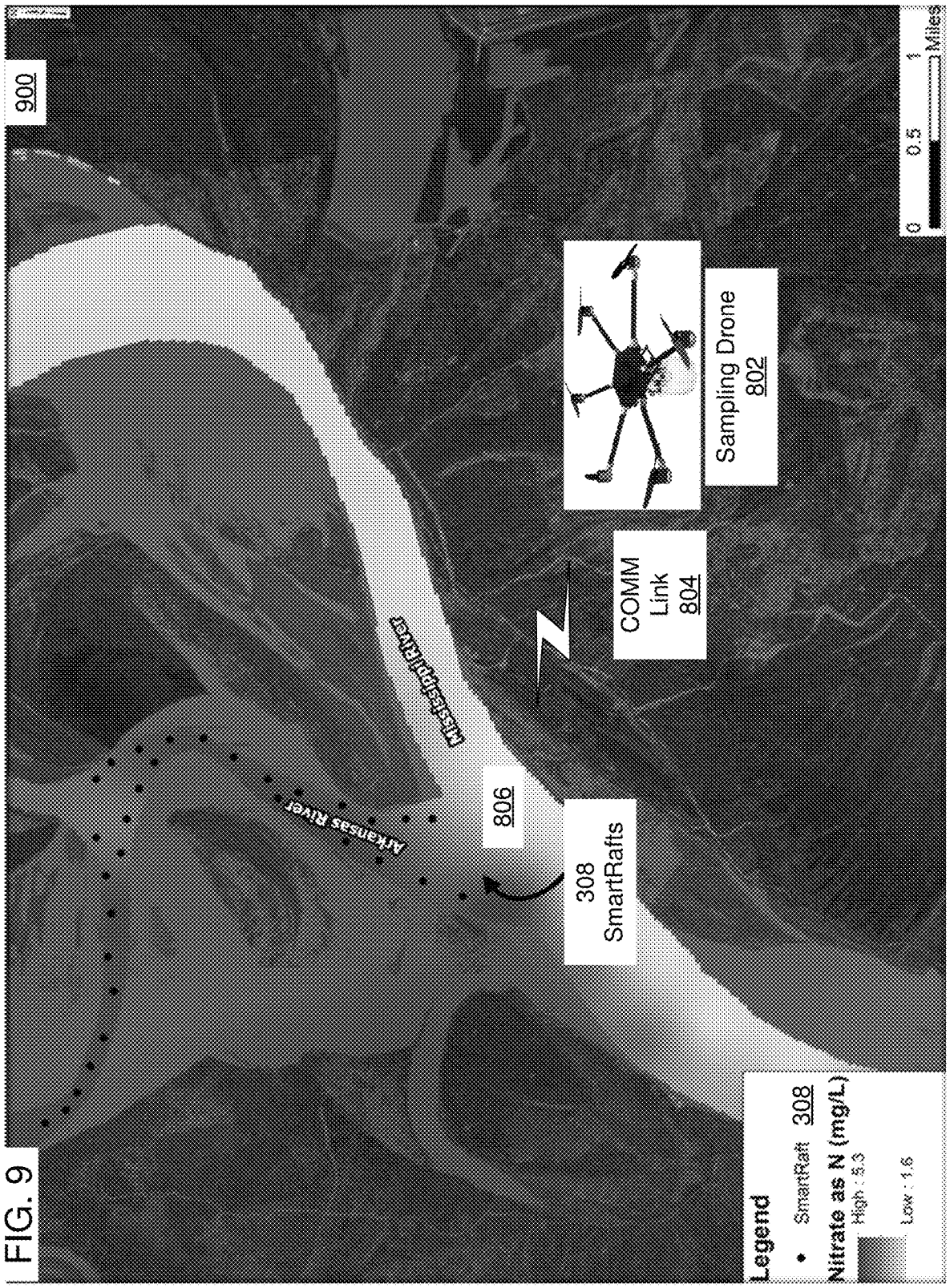
FIG. 9 is a diagram showing an array of smart rafts deployed in treatment phase at the direction of a sampling drone.

FIG. 9 is a diagram showing an array of smart rafts deployed in treatment phase at the direction of a sampling drone. In FIG. 9, the system 900 includes an array of the smart rafts 308 deployed in the "treatment phase" at the direction of the sampling drones 802 to remove pollutants of concern, and the like, through on-site or in situ bioremediation or phytoremediation, and the like. In the "treatment phase," the smart rafts or groups of smart rafts 308 are deployed in areas where water quality conditions of concern were observed and are predicted based on what was learned during deployment in the "evaluation phase," as shown in FIG. 8. The smart rafts 308 can be dynamically deployed to iteratively target pollutants of concern as the process of monitoring continues during bioremediation and phytoremediation processes. For example, a cluster of the smart rafts 308 are deployed in the Arkansas River to remove elevated nitrate before it enters the Mississippi River. For a given application, suitable water quality sensors can be employed to track reductions in observed nitrate concentrations, and the like, and can redeploy individual rafts or clusters of rafts 308 to other areas, once a target or desired water quality condition is achieved.

Advantageously, the sampling drones 802 are able to continuously screen water quality, and the like, while the smart rafts 308 are deployed in the "treatment phase" to guide subsequent deployment at target locations, and the like. The fast-moving drones 802 allow for efficient screening of water quality conditions and allow for the deployment of the smart rafts 308, for example, in areas where conditions are variable or less understood, and the like. Advantageously, the drones 802 are able to continue screening water quality, and the like, while the smart rafts 308 are deployed in the "treatment phase" to guide subsequent deployment at target locations, and like.

The above-described devices and subsystems of the illustrative embodiments can include, for example, any suitable servers, workstations, PCs, laptop computers, PDAs, Internet appliances, handheld devices, cellular telephones, wireless devices, other devices, and the like, capable of performing the processes of the illustrative embodiments. The devices and subsystems of the illustrative embodiments can communicate with each other using any suitable protocol and can be implemented using one or more programmed computer systems or devices.

One or more interface mechanisms can be used with the illustrative embodiments, including, for example, Internet access, telecommunications in any suitable form (e.g., voice, modem, and the like), wireless communications media, and the like. For example, employed communications networks or links can include one or more wireless communications networks, cellular communications networks, G3 communications networks, Public Switched Telephone Network (PSTNs), Packet Data Networks (PDNs), the Internet, intranets, a combination thereof, and the like.

It is to be understood that the devices and subsystems of the illustrative embodiments are for illustrative purposes, as many variations of the specific hardware used to implement the illustrative embodiments are possible, as will be appreciated by those skilled in the relevant art(s). For example, the functionality of one or more of the devices and subsystems of the illustrative embodiments can be implemented via one or more programmed computer systems or devices.

To implement such variations as well as other variations, a single computer system can be programmed to perform the special purpose functions of one or more of the devices and subsystems of the illustrative embodiments. On the other hand, two or more programmed computer systems or devices can be substituted for any one of the devices and subsystems of the illustrative embodiments. Accordingly, principles and advantages of distributed processing, such as redundancy, replication, and the like, also can be implemented, as desired, to increase the robustness and performance of the devices and subsystems of the illustrative embodiments.

The devices and subsystems of the illustrative embodiments can store information relating to various processes described herein. This information can be stored in one or more memories, such as a hard disk, optical disk, magneto-optical disk, RAM, and the like, of the devices and subsystems of the illustrative embodiments. One or more databases of the devices and subsystems of the illustrative embodiments can store the information used to implement the illustrative embodiments of the present inventions. The databases can be organized using data structures (e.g., records, tables, arrays, fields, graphs, trees, lists, and the like) included in one or more memories or storage devices listed herein. The processes described with respect to the illustrative embodiments can include appropriate data structures for storing data collected and/or generated by the processes of the devices and subsystems of the illustrative embodiments in one or more databases thereof.

All or a portion of the devices and subsystems of the illustrative embodiments can be conveniently implemented using one or more general purpose computer systems, microprocessors, digital signal processors, micro-controllers, and the like, programmed according to the teachings of the illustrative embodiments of the present inventions, as will be appreciated by those skilled in the computer and software arts. Appropriate software can be readily prepared by programmers of ordinary skill based on the teachings of the illustrative embodiments, as will be appreciated by those skilled in the software art. Further, the devices and subsystems of the illustrative embodiments can be implemented on the World Wide Web. In addition, the devices and subsystems of the illustrative embodiments can be implemented by the preparation of application-specific integrated circuits or by interconnecting an appropriate network of conventional component circuits, as will be appreciated by those skilled in the electrical art(s). Thus, the illustrative embodiments are not limited to any specific combination of hardware circuitry and/or software.

Stored on any one or on a combination of computer readable media, the illustrative embodiments of the present inventions can include software for controlling the devices and subsystems of the illustrative embodiments, for driving the devices and subsystems of the illustrative embodiments, for enabling the devices and subsystems of the illustrative embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the illustrative embodiments of the present inventions can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the illustrative embodiments of the present inventions can be distributed for better performance, reliability, cost, and the like.

As stated above, the devices and subsystems of the illustrative embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present inventions have been described in connection with a number of illustrative embodiments, and implementations, the present inventions are not so limited, but rather cover various modifications, and equivalent arrangements, which fall within the purview of the appended claims.

What is claimed is:

1. A system for monitoring and improving water quality to mitigate harmful algal blooms using smart rafts, the system comprising:
   a controllable raft made from a mycomaterial;
   one or more tube-shaped pods formed in the raft and comprising a root channel at the bottom of the pods extending through a bottom of the raft;
   a water channel extending through a bottom of the raft;
   a water quality sensor configured to sense nitrate ions, temperature, precipitation levels, and phytoextraction and phytostabilization of metals, and generate sensor information based on same;
   a microcontroller configured to receive sensor information from the water quality sensor and deploy the raft based on the water quality sensor;
   a sensor holder formed in the raft and configured to hold the water quality sensor to allow for accessing the water channel
   wherein remedial plants are grown in the tube-shaped pods with roots of the remedial plants passing through the water channel into water underneath the raft;
   a sampling drone comprising liquid sample receptacles configured to capture multiple liquid samples from a water body, the sampling drone in communication with the controllable raft via a communication link; and
   the sampling drone configured to screen the water quality conditions and deploy the controllable raft to targeted locations.

2. The system of claim 1, further comprising:
   a surface camera mounted in top of the raft for providing one of media documentation, surveillance, and status information.

3. The system of claim 1, further comprising:
   an underwater camera mounted underneath the raft for providing visual information of water quality.

4. The system of claim 1, further comprising:
   one or more solar panels mounted on the raft serving as a power source for electronic elements.

5. The system of claim 1, further comprising:
   a global positioning system (GPS) mounted on the raft providing positional information.

6. The system of claim 1, further comprising:
   a motor mounted on the raft to drive a propulsion system to actively move and position of the raft.

7. The system of claim 1, further comprising:
   a propulsion system mounted on the raft to provide for controlled movement of the raft.

8. The system of claim 1, further comprising:
   a rudder to steer the raft into desired positions.

9. The system of claim 1, further comprising:
   a coupling device to allow one or more rafts to be connected and disconnected to one another.

10. The system of claim 1, further comprising:
    one or more rafts deployable across a body of water to evaluate water quality conditions.

11. The system of claim 1, further comprising:
    one or more rafts deployable in targeted locations within a body of water to improve water quality conditions.

12. The system of claim 1, further comprising:
    wherein the controllable raft further comprises an array of the rafts,
    wherein the sampling drone further comprises one or more sampling drones, wherein the array of the rafts is deployable under direction of the one or more sampling drones.

13. A system for monitoring and improving water quality to mitigate harmful algal blooms using smart rafts, the system comprising:
    one or more rafts, each raft made from a mycomaterial;
    one or more tube-shaped pods formed in the raft, evenly distributed throughout the entire raft, comprising a root channel at the bottom of the pods extending through a bottom of the raft;
    a water channel extending through a bottom of each raft;
    a water quality sensor on each raft;
    a sensor holder formed in each raft and configured to hold the water quality sensor accessing the water channel, wherein the sensor is configured to sense nitrate ions, precipitation levels, temperature, and phytoextraction and phytostabilization of metals, and generate sensor information based on same, a microcontroller on each raft configured to receive sensor information from the water quality sensor and deploy the raft based on the water quality sensor;

wherein remedial plants are grown in the tube-shaped pods with roots of the remedial plants passing through the water channel into water underneath the raft;

a surface camera mounted on top of each raft for providing one of media documentation, surveillance, and status information;

an underwater camera mounted underneath each raft for providing visual information of water quality;

one or more solar panels mounted on each raft serving as a power source for electronic elements;

a global positioning system (GPS) mounted on each raft providing positional information;

a motor mounted on each raft to drive a propulsion system to actively move and position of the raft;

the propulsion system mounted on each raft to provide for controlled movement of the raft;

a rudder to steer each raft into desired positions;

a coupling device to allow one or more rafts to be connected and disconnected to one another, wherein the one or more rafts are deployable across a body of water to evaluate water quality conditions and generate respective sensor information, and wherein the one or more rafts are deployable in targeted locations within a body of water to improve water quality conditions and generate respective sensor information; and one or more sampling drones comprising liquid sample receptacles configured to capture multiple liquid samples from a water body, the sampling drone in communication with each raft via a communication link, the sampling drone configured to screen the water quality conditions and deploy the controllable raft to targeted locations.

\* \* \* \* \*